US007010345B2

(12) United States Patent
Hill et al.

(10) Patent No.: US 7,010,345 B2
(45) Date of Patent: Mar. 7, 2006

(54) METHOD AND APPARATUS TO MINIMIZE EFFECTS OF A CARDIAC INSULT

(75) Inventors: Michael R. S. Hill, Minneapolis, MN (US); Gary W. King, Fridley, MN (US); Thomas J. Mullen, Ham Lake, MN (US); Xiaohong Zhou, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 236 days.

(21) Appl. No.: 09/999,723

(22) Filed: Oct. 26, 2001

(65) Prior Publication Data

US 2002/0143369 A1 Oct. 3, 2002

Related U.S. Application Data

(60) Provisional application No. 60/294,072, filed on May 29, 2001, provisional application No. 60/243,609, filed on Oct. 26, 2000, provisional application No. 60/243,536, filed on Oct. 26, 2000, provisional application No. 60/243,393, filed on Oct. 26, 2000.

(51) Int. Cl.
*A61N 1/18* (2006.01)
(52) U.S. Cl. ............................................. 607/10; 607/9
(58) Field of Classification Search ................ 600/373, 600/377, 509, 515, 516, 518, 519, 521; 607/6, 607/7, 9, 10, 11, 14, 25, 48, 117, 118
See application file for complete search history.

(56) References Cited

U.S. PATENT DOCUMENTS

| 3,421,511 | A | | 1/1969 | Schwartz et al. | 128/418 |
|---|---|---|---|---|---|
| 3,645,267 | A | | 2/1972 | Hagfors | 128/421 |
| 3,650,277 | A | | 3/1972 | Sjostrand et al. | 128/419 C |
| 3,796,221 | A | | 3/1974 | Hagfors | 128/421 |
| 4,458,696 | A | | 7/1984 | Larimore | 128/798 |
| 4,694,835 | A | | 9/1987 | Strand | 128/640 |
| 5,031,618 | A | | 7/1991 | Mullett | 128/421 |
| 5,058,584 | A | | 10/1991 | Bourgeois | 128/421 |
| 5,135,004 | A | | 8/1992 | Adams et al. | 128/696 |
| 5,199,428 | A | | 4/1993 | Obel et al. | 128/419 |
| 5,251,621 | A | * | 10/1993 | Collins | 607/4 |
| 5,330,505 | A | * | 7/1994 | Cohen | 607/6 |
| 5,330,507 | A | | 7/1994 | Schwartz | 607/14 |
| 5,330,515 | A | | 7/1994 | Rutecki et al. | 607/46 |
| 5,342,409 | A | | 8/1994 | Mullett | 607/46 |

(Continued)

FOREIGN PATENT DOCUMENTS

EP 0688577 12/1995

*Primary Examiner*—Robert E. Pezzuto
*Assistant Examiner*—Frances P. Oropeza
(74) *Attorney, Agent, or Firm*—Paul H. McDowall; Girma Wolde-Michael

(57) ABSTRACT

A method and apparatus are provided for protecting cardiac tissue from insult. The method comprises identifying the occurrence of an insult, such as a heart attack, and delivering electrical stimulation to one or more predetermined nerves in a patient's body in response to identifying the occurrence of the insult. The stimulation may be provided at the spinal canal or on the chest wall of the patient through cutaneous electrodes.

25 Claims, 11 Drawing Sheets

U.S. PATENT DOCUMENTS

| | | | |
|---|---|---|---|
| 5,496,363 A | 3/1996 | Burgio et al. | 607/152 |
| 5,700,282 A | 12/1997 | Zabara | 607/9 |
| 5,702,429 A * | 12/1997 | King | 607/46 |
| 5,776,170 A * | 7/1998 | MacDonald et al. | 607/46 |
| 5,817,131 A * | 10/1998 | Elsberry et al. | 607/5 |
| 5,824,021 A | 10/1998 | Rise | 607/46 |
| 6,058,331 A | 5/2000 | King | 607/62 |
| 6,134,470 A | 10/2000 | Hartlaub | 607/14 |
| 6,587,726 B1 * | 7/2003 | Lurie et al. | 607/42 |
| 6,885,888 B1 * | 4/2005 | Rezai | 607/9 |

\* cited by examiner

METHOD AND APPARATUS TO MINIMIZE EFFECTS OF A CARDIAC INSULT

RELATED CASES

This case claims priority to the following provisionally-filed cases:

U.S. Provisional Patent Application Ser. No. 60/294,072, filed May 29, 2001, entitled "Closed-Loop Neuromodulation for Prevention and Treatment of Cardiac Conditions";

U.S. Provisional Patent Application Ser. No. 60/243,393, filed Oct. 26, 2000, entitled "Method and Apparatus to Minimize the Effects of a Cardiac Insult";

U.S. Provisional Patent Application Ser. No. 60/243,536, filed Oct. 26, 2000, entitled "Method and Apparatus to Minimize the Effects of a Cardiac Insult"; and U.S. Provisional Patent Application Ser. No. 60/243,609, filed Oct. 26, 2000, entitled "Method and Apparatus for Electrically Simulating the Nervous System to Improve Ventricular Dysfunction, Heart Failure, and Other Cardiac Conditions", all of which are incorporated herein by reference in their entireties.

This case is related to, and contains subject matter in common with the following applications:

U.S. patent application Ser. No.09/999,723 filed on Oct. 26, 2001 entitled "Method and Apparatus to Minimize the Effects of a Cardiac Insult; "

U.S. patent application Ser. No. 10/035,319 filed on Oct. 26, 2001 entitled "Closed-Loop Neuromodulation for Prevention and Treatment of Cardiac Conditions; "

U.S. patent application Ser. No.10/039,307 filed on Oct. 26, 2001 entitled "Method and Apparatus for Electrically Stimulating The Nervous System to Improve Ventricular Dysfunction, Heart Failure, and Other Cardiac Conditions; "

FIELD OF THE INVENTION

This invention relates generally to a method and apparatus for electrically stimulating select nerves to alter conditions within the heart, and, more particularly, to nerve stimulation to protect myocardium acutely, and to reduce anginal pain by stimulating cutaneous tissue.

DESCRIPTION OF THE RELATED ART

Various cardiac conditions, such as supraventricular arrhythmias, angina pectoris, and ventricular dysfunction or heart failure, have been treated by electrical stimulation of the spinal cord, vagus and other nerves. Typically, electrodes are implanted in the patient adjacent the spinal area and electrically excited to produce desirable effects on the functioning of the heart. For example, a paper entitled "Vagal Tuning" by Bilgutay et. al., published in the Journal of Thoracic and Cardiovascular Surgery, Vol. 56, No. 1, July 1968, pp. 71–82, discusses a system that delivers electrical stimulation to the vagus nerve using silastic coated, bipolar electrodes, such as those described in U.S. Pat. No. 3,421,511. The electrodes are surgically implanted around the intact nerve or nerves and a controlled current is delivered thereto. The electrodes pass the current to the nerve(s), producing a decreased heart rate while still preserving sinus rhythm in the patient. Low amplitude stimulation has also been employed to control induced tachycardias and ectopic beats.

Angina pectoris and paroxysmal atrio-ventricular junctional or supraventricular tachycardias have also been treated by stimulating the carotid sinus nerve via implanted electrodes. For example, a paper entitled "Carotid Sinus Nerve Stimulation in the Treatment of Angina Pectoris and Supraventricular Tachycardia," published in California Medicine, 112:41–50, March 1970, describes a system in which patients may electrically stimulate their carotid sinus nerve when they sense angina and/or supraventricular tachycardia.

Delivery of electrical stimulation to the nervous system using an implanted electrode has been found particularly effective in the relief of chest pain, such as angina pectoris, that often accompanies myocardial ischemia. For example, U.S. Pat. No. 5,058,584 to Bourgeois, incorporated herein by reference in its entirety, discloses a system and method for treating such chest pain using electrical stimulation within the epidural space of the spinal cord. This treatment is provided only after a symptomatic level of activity is reached as sensed by an accelerometer or other activity sensor. Similarly, U.S. Pat. No. 6,058,331 to King, also incorporated herein by reference in its entirety, discusses a system and method for treating ischemia by automatically adjusting electrical stimulation to the spinal cord, peripheral nerve, or neural tissue ganglia based on a sensed patient condition. U.S. Pat. No. 5,199,428 to Obel et al., incorporated herein by reference in its entirety, discloses a system for stimulating the epidural space with continuous and/or phasic electrical pulses using an implanted pulse generator upon the detection of myocardial ischemia to decrease cardiac workload, and thereby reduce cell death related to the ischemic event U.S. Pat. No. 5,824,021 to Rise, incorporated herein by reference in its entirety, discusses a system and method for providing spinal cord stimulation to relieve angina, and to further provide a patient notification that an ischemic event is occurring This spinal cord stimulation is provided only after the ischemia is already detected.

In addition to the above-described systems, other systems have been disclosed to provide nerve stimulation following the onset of predetermined condition. U.S. Pat. No. 6,134,470 to Hartlaub describes a system for utilizing spinal cord stimulation to terminate tachyarrhythmias. The stimulation is provided only after the tachyarrhythmias, or a precursor thereto, has been detected U.S. Pat. No. 3,650,277 discloses a system for stimulating the left and right carotid sinus nerves in response to the detection of elevated mean arterial blood pressure to alleviate hypertension.

Each of the nerve stimulation systems described above have at least one significant drawback. For example, these nerve stimulation systems rely upon electrodes that are surgically implanted adjacent the spine. Successful placement of the electrodes in the region surrounding the spine requires substantial surgical expertise. Emergency personnel, however, do not commonly possess this expertise, nor do they often have the equipment or environment suitable for the task. Thus, while emergency personnel may be summoned to transport an afflicted patient to a hospital and, thus, are the first medical personnel to administer aid to the patient, they may not be capable of implanting the electrodes. Without the implanted electrodes, the therapeutic stimulation may not be immediately provided. Rather, application of the therapy is delayed until the patient arrives at an appropriate medical facility.

The present invention is directed to overcoming, or at least reducing the effects of, one or more of the problems set forth above.

SUMMARY OF THE INVENTION

The current invention involves a neuromodulation system to provide stimulation to at least a portion of the nervous system of the body. The stimulation is provided using one or more electrodes placed adjacent an external surface of the body. The stimulation is provided in anticipation or detection of a cardiac insult, wherein "cardiac insult" in this context is intended to include, but is not limited to, mechanical, chemical, or electrical impairment or damage of cardiac tissue due to conditions such as heart failure, ventricular tachycardia, supraventricular tachycardia, ischemia, imbalance of autonomic tone, or the like.

In one embodiment, the current invention provides a system and method to provide stimulation at locations adjacent the spinal region and on the chest wall. Such stimulation has been shown to improve cardiac function, to limit ischemic attacks, to reduce sympathetic activity of the cardiac tissue, and to reduce the likelihood and/or the severity of ventricular arrhythmia. Thus, the electrical stimulation produces effects similar to those induced by prescription beta-blocker drugs. This type of stimulation has been shown to reduce cardiac work, improve heart function, vasodilate peripheral arterioles and increase blood flow to the limbs.

According to the invention, one or more electrodes may be placed cutaneously adjacent one or more of the T1–T12 vertebrae, with the T1–T4 locations being preferred. Alternatively, the electrodes may be placed adjacent the chest wall or anywhere within a region of the T1–T5 dermatomes. The position of the electrodes may be, for example, in the pectoral region of the left chest located beneath the facia on the muscle and motor point of the pectoral muscle with stimulation of the musculocutaneous and thoracic nerves. In another example, the electrodes may be positioned in the auxiliary region beneath the left arm with stimulation provided to the musculocutaneous, brachialcutaneous and thoracodorsal nerves. Because cutaneous electrodes are utilized, a surgeon is not needed to perform the procedure. Rather, any person may initiate the stimulation by merely positioning the electrodes adjacent one or more surfaces of the body.

According to one aspect of the invention, the invention delivers electrical stimulation when the system is activated by a patient or other person such as a health care provider. For example, a medical care provider such as a paramedic may initiate stimulation to treat a patient that is having a heart attack. The patient himself may initiate such therapy if the onset of a heart attack is suspected. Studies have shown that this can prevent arrhythmias, fibrillation, and cell death, possibly by reducing sympathetic activity in the heart. A patient may alternatively initiate stimulation in anticipation of undergoing exercise. A surgeon may initiate stimulation in anticipation of performing a surgical procedure such as the insertion of a stent, or any other procedure that may disrupt cardiac tissue. Nerve stimulation may be manually initiated by a paramedic after a high-voltage shock is delivered to a patient. Such stimulation stabilizes the heart and prevents the re-occurrence of fibrillation or an arrhythmia. Such stimulation may continue throughout the insult, and may optionally continue for a predetermined period of time following the insult.

According to another embodiment, the inventive system may be operated in a closed-loop mode. In this mode, one or more physiological parameters may be sensed using physiological sensors. The sensed physiological signals may be used to predict or detect the onset of an insult. These signals may also be used to modulate delivery of the stimulation parameters such as pulse width, amplitude, frequency, and the like.

According to yet another embodiment, the inventive system stores data signals indicative of past electrical stimulation so that future stimulation may be optimized. This stored data may also be used by healthcare professionals in the treatment and diagnosis of the condition.

According to another aspect of the instant invention, a method is provided for protecting cardiac tissue from insult. The method comprises identifying a future or current cardiac insult, and delivering cutaneous electrical stimulation to one or more predetermined nerves in a patient's body in response to identifying the occurrence of the insult.

In another aspect of the instant invention, an apparatus is provided for protecting cardiac tissue from insult. The apparatus is comprised of at least one electrode positionable at a region adjacent to a surface of a patient's body proximate nervous tissue, and a controller adapted to deliver electrical stimulation to the electrodes for a period of time in relation to the onset of an insult.

Figure 1A:
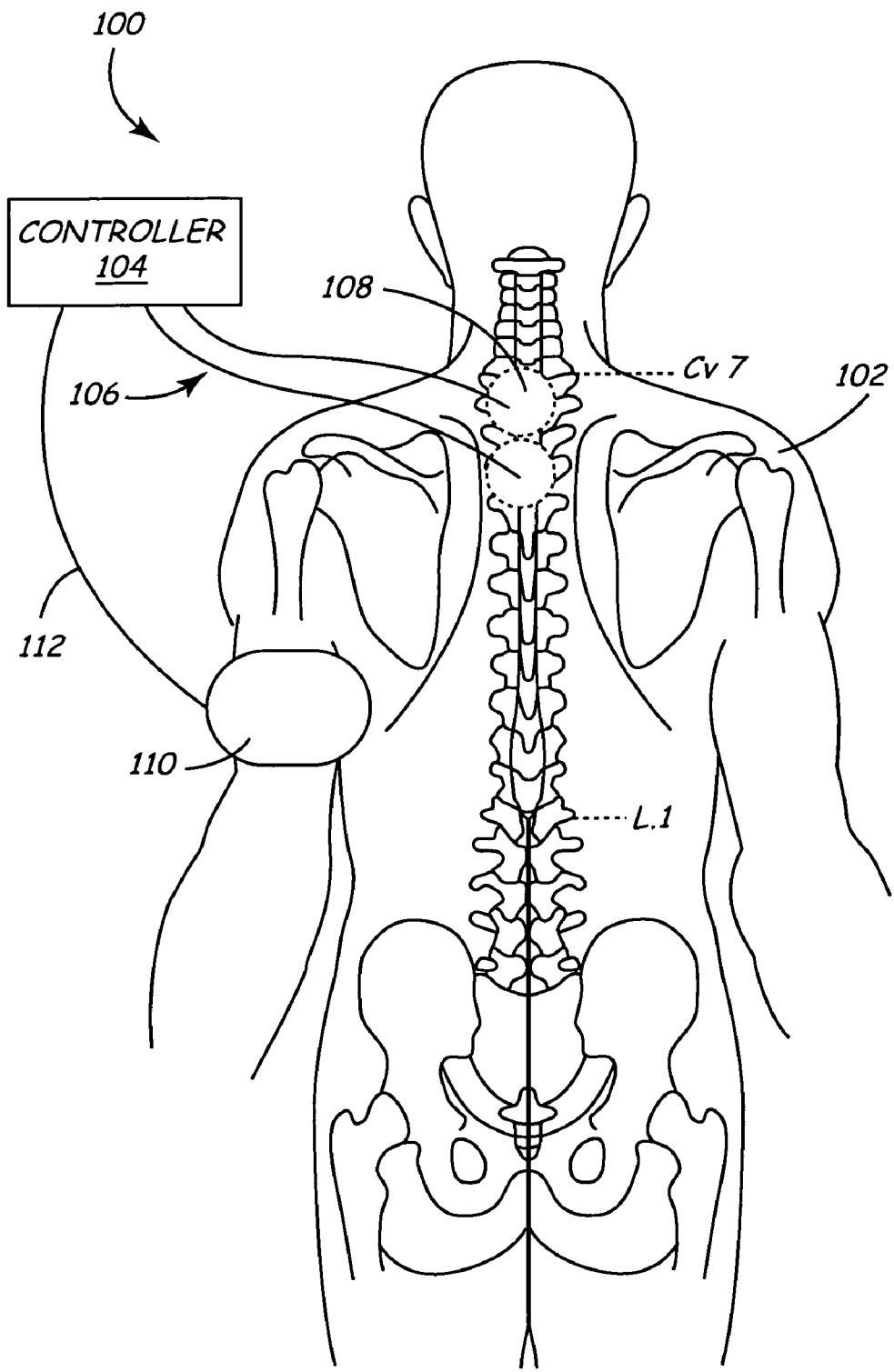
FIG. 1A illustrates a stylized representation of a posterior view of a patient with electrodes positioned thereon.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Illustrative embodiments of a method and apparatus for providing improved cardiac function according to the present invention are shown in the Figures. As will be readily apparent to those skilled in the art upon a complete reading of the present application, the present method and apparatus are applicable to a variety of systems other than the embodiment illustrated herein.

The method and apparatus described herein provides many of the benefits previously only available from systems utilizing implanted electrodes to accomplish neutral stimulation. That is, cutaneous stimulation that avoids surgical procedures adjacent the spinal area, have unexpectedly shown to favorably produce many of the benefits previously only associated with neural stimulation.

Figure 1B:
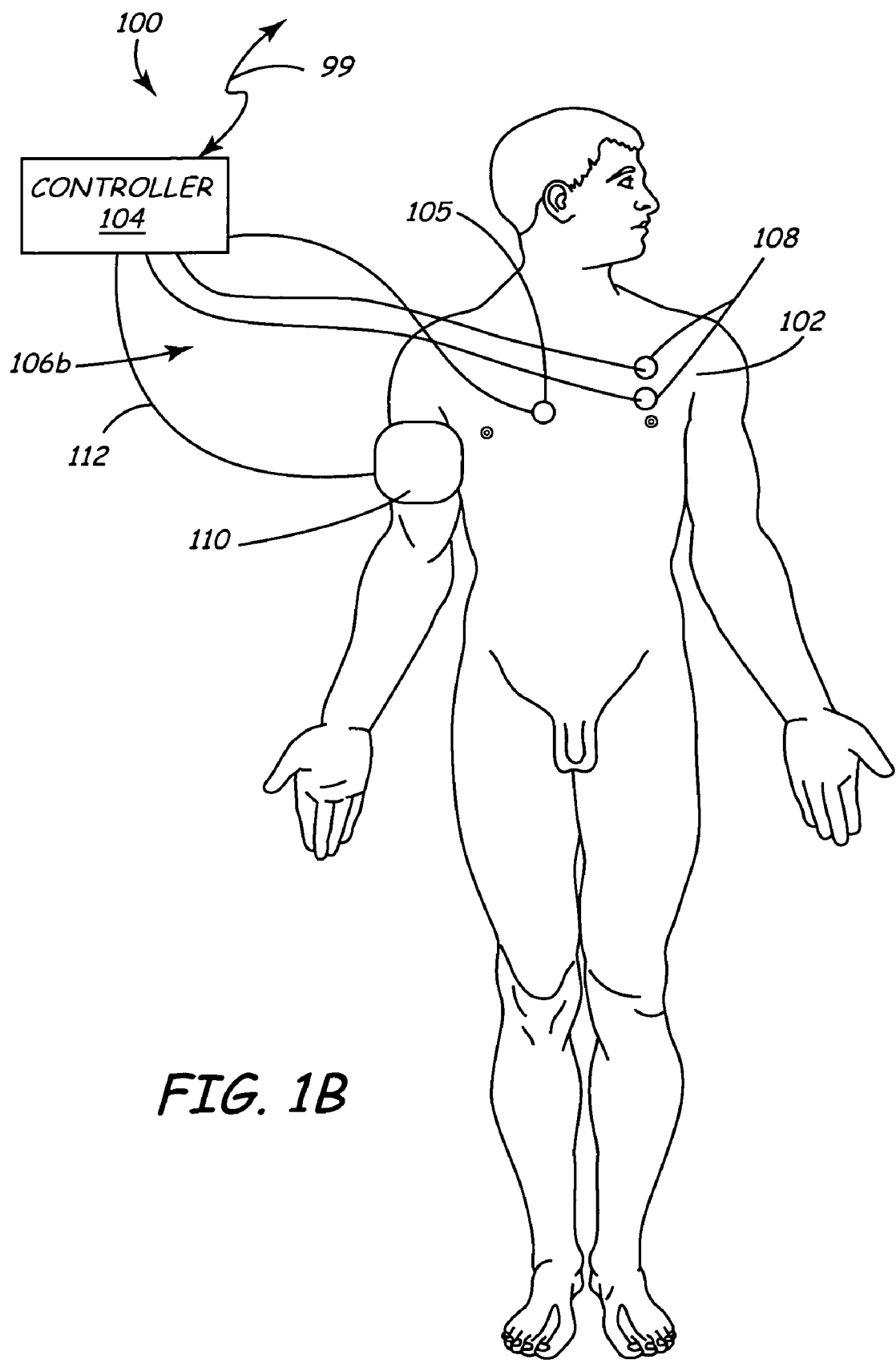
FIG. 1B illustrates a stylized representation of an anterior view of a patient with electrodes positioned thereon.

Generally, the instant invention is directed to a method and apparatus for minimizing the infarcted area during a heart attack or coronary artery intervention, preventing arrhythmias, and limiting anginal attacks. In the illustrated embodiment, the current invention utilizes cutaneous electrical stimulation to treat ventricular dysfunction, heart failure, ischemia, arrhythmia, etc. As shown in FIGS. 1A and 1B, a system 100 provides stimulation to a patient 102 at locations adjacent the spinal region and on the chest wall, respectively. Such stimulation has been shown to improve cardiac function, to limit ischemic attacks, to reduce sympathetic activity of the cardiac tissue, to reduce the likelihood and/or the severity of ventricular arrhythmia. Thus, the electrical stimulation produces effects similar to those induced by prescription beta-blocker drugs. This type of stimulation has been shown to reduce cardiac work, improve heart function, vasodilate peripheral arterioles and increase blood flow to the limbs. The stimulation may further cause the production of neuropeptides such as CGRP, NO, and VIP that are known vasodilators, which may assist in redirection of blood flow from regions of high flow to regions of low flow. This further improves the efficiency of the heart. In ischemic dilated cardiomyopathy patients, this therapy may suppress or reduce subendocardial ischemia, and hence be cardio-protective. Electrical stimulation may further result in improvements in operation/efficiency and function of cardiac tissue, even in the absence of an adequate blood supply.

The electrodes 108 may take on any of a variety of forms, including but not limited to conventional surface mounted electrodes, such as are commonly used in conjunction with Transcuteous Electrical Neurological Stimulator (TENS) units. These surface mounted electrodes may be fixed to the patient 102 via any of a variety of conventional mechanical or chemical mechanisms or may be simply held in place by friction and gravity Any electrodes and associated circuitry known in the art for in conjunction with cutaneously stimulation may be adapted for use within the current invention. Such systems are disclosed, for example, in U.S. Pat. Nos. 4,694,835, 4,458,696, and 5,496,363.

A controller 104 is coupled through conventional conductive links 106, such as leads or wires, to one or more of the cutaneous electrodes 108 mounted in various regions of a patient's body. For example, the electrodes 108 may be applied cutaneously adjacent one or more of the T1–T12 vertebrae, with the T1–T4 locations being preferred. Alternatively, the electrodes may be placed adjacent the chest wall (see FIG. 1B) or anywhere within a region of the T1–T5 dermatomes (i.e., the regions of the body innervated by nerves originating from or projecting to T1–T5). The position of the electrode may be, for example, in the pectoral region of the left chest located beneath the facia on the muscle and motor point of the pectoral muscle with stimulation of the musculocutaneous and thoracic nerves. In another example, the electrodes may be positioned in the axillary region beneath the left arm with stimulation provided to the musculocutaneous, brachialcutaneous and thoracodorsal nerves. In this position, the electrode will provide neural traffic into the same dermatome as the typical anginal pain/heart attack pain.

The controller 104 may take the form of an external device or an implantable device. Where the controller 104 is an external device, it may be useful in providing therapeutic signals to a patient who is experiencing an unexpected cardiac event, such as a first or otherwise unanticipated episode of ventricular dysfunction or ischemic attack.

The controller 104 may be programmed for either automatic or manual operation. In manual mode, the controller begins stimulation in response to a manual trigger. This manual trigger may be a switch or any other type of user interface, including a voice-activated interface, or a touch-activated interface. This trigger could be activated by a patient, or a health care provider, for example. If desired, the activation could be accomplished remotely using a telephone link or other communication link. The activation could be password or otherwise protected, if desired.

Manual activation of stimulation may be prompted by a variety of situations. For example, a medical care provider such as a paramedic may initiate stimulation to treat a patient that is having a heart attack. The patient himself may initiate such therapy if the onset of a heart attack is suspected. Studies have shown that this can prevent arrhythmias, fibrillation, and cell death, possibly by reducing sympathetic activity in the heart. A patient may alternatively initiate stimulation in anticipation of undergoing exercise. A surgeon may initiate stimulation in anticipation of performing a surgical procedure such as the insertion of a stent, or any other procedure that may disrupt cardiac operation. Such anticipatory delivery of cardiac stimulation has been determined by the Applicants to minimize damage of cardiac myocytes due to a subsequent ischemic event. Nerve stimulation may be manually initiated by a paramedic after a high-voltage shock is delivered to a patient. Such stimulation stabilizes the heart and prevents the re-occurrence of fibrillation or an arrhythmia. Any other anticipated or occurring cardiac insult may prompt a healthcare provider or patient to trigger controller 104 to initiated stimulation via the one or more electrodes. Such stimulation may continue throughout the insult, and may optionally continue for a predetermined period of time following the insult. These embodiments are based on data obtained through research conducted over several years involving electrical stimulation to reduce angina.

In another instance, stimulation could be provided at a sub-threshold level for paresthesia during the delivery of the defibrillation shock to reduce the perceived pain associated with the arrhythmia and the shock and stabilize the heart and help prevent re-occurrence of the arrhythmia. Alternatively, percutaneous stimulation could be performed for a week or more to provide cardiac stabilization.

In one embodiment, cutaneous electrical stimulation of the spinal cord at locations T1–T4 is performed prior to a patient engaging in exercise. Such stimulation appears to result in a short-term inhibition of the sympathetic outflow of the heart, which in turn causes changes in the neural chemistry in a manner that prevents damage from ischemic conditions. Stimulation may be provided for a predetermined length of time, which in one embodiment is approximately thirty minutes, shortly prior to performing the cardiac procedure or engaging in exercise. The amount of stimulation may also be selected based on the anticipated level of exertion.

In another embodiment, cutaneous electrical stimulation may be performed at upper cervical levels C1–C4 over back of the head and neck instead of at T1–T4. Although stimulation of this area has typically been performed to reduce jaw and neck pain, it has been found such stimulation, can also reduce angina, and can provide important cardiac protection when performed prior to a cardiac insult.

In one embodiment the controller may also initiate stimulation automatically. For example, nerve stimulation may be automatically initiated by an automatic external defibrillator (AED) following the delivery of a high-voltage shock to stabilize the heart in a manner discussed above.

In another embodiment, stimulation may be automatically initiated because of physiological measurements obtained by the controller 104. That is, the controller 104 may have one or more conventional sensors (not shown) of a type capable of sensing a cardiac event in the patient. This may include, for example, externally-placed electrodes such as electrode 105 for measuring ECG signals in a manner known in the art. Other sensors such as sensor 110 may be positioned adjacent the body of the patient 102 to sense various physiological conditions, which are communicated back to the controller 104 over leads 112. The measured physiological conditions may be used to initiate stimulation. For example, a blood pressure, temperature, and/or any other externally-positionable sensors known in the art may also be coupled to controller 104. If the patient has an implantable medical device including an internal sensor and a communication circuit such that sensor measurements may be transferred to controller 104, the measurements obtained from these internal sensors may also be utilized by controller 104 for automatic operation.

In addition to initiating the delivery of stimulation, sensor measurements may be used to control parameters associated with the stimulation. For example, the measured physiological conditions may be used as an indication of the patient's response to the therapy being administered by the controller 104. A positive physiological response may be used as an indication that the therapy is achieving the desired result. The sensed physiological conditions may be used to adjust the parameters of the stimulation. For example, the controller 104 may measure and record cardiac pulse pressure. A change in the cardiac pulse pressure or ST segment change or arrhythmic beats may be used in a closed-loop system to adjust delivery of stimulation. For example, if the controller 104 detects that the cardiac pulse pressure has declined over time, then the parameters of the stimulation may be adjusted in an attempt to increase the cardiac pulse pressure. On the other hand, where the controller 104 observes a consistent, appropriate cardiac pulse pressure, then the stimulation may be continued, as a desired result is being achieved by the stimulation. Where the controller 104 observes continued high, or even rising, cardiac pulse pressure, then the parameters of the stimulation may be adjusted in an attempt to reduce ST segment depression/elevation or reduce incidences of arrhythmic beats.

Other parameters that may be measured and used as feedback in a closed loop control system for the SCS include, but are not limited to, pressure-volume (PV) loops, pressure-area (PA) loops, pressure-dimension (PD) loops, diastolic and systolic pressures, estimated pulmonary artery pressure, change in cardiac pulse pressure over time, pre-ejection timing intervals, ST segment changes, heart rate changes, arrhythmic counts, and blood chemical measurements. Any combination of the foregoing may be used to determine the timing, waveforms, and amplitude of the electrical stimulation delivered to the electrodes 108. Those skilled in the art will appreciate that the illustrated, representative sensor 110 may take on any of a variety of forms, depending upon the physiological parameter being sensed. Generally, these feedback parameters may be detected and used to control certain parameters of the stimulation, such as the magnitude, duration and frequency. Typically, the stimulation falls within the range of about 200–400 microsecond duration pulses, at a frequency in the range of about 50–100 Hz, and at a voltage of up to about 20–60V, although other voltage amplitudes and frequencies may be used. For example, with greater stimulation parameters (increased magnitude, increased frequency and/or increased pulse durations, there is a potential for greater beta-blocker type (withdrawal of sympathetic activity) effect. This would result in reduced heart rate, alteration in blood flow (increase in coronary supply), improved cardioprotection and decreased workload or demand. An additional example is the appropriate use of pre-set parameters in response to sensed cardiac event information of the patient. For example, if the patient is having a decompensation ventricular dysfunction or heart failure event, then "more strenuous" stimulation parameters may be used to provide the greatest amount of protection and local withdrawal of sympathetic activity (e.g. increased magnitude, increased pulse width and increased frequency). For a less severe event, such as an elevation in end diastolic pressure, then "less strenuous" stimulation parameters may be used to provide an incremental adjustment to the cardiac function.

Figure 2:
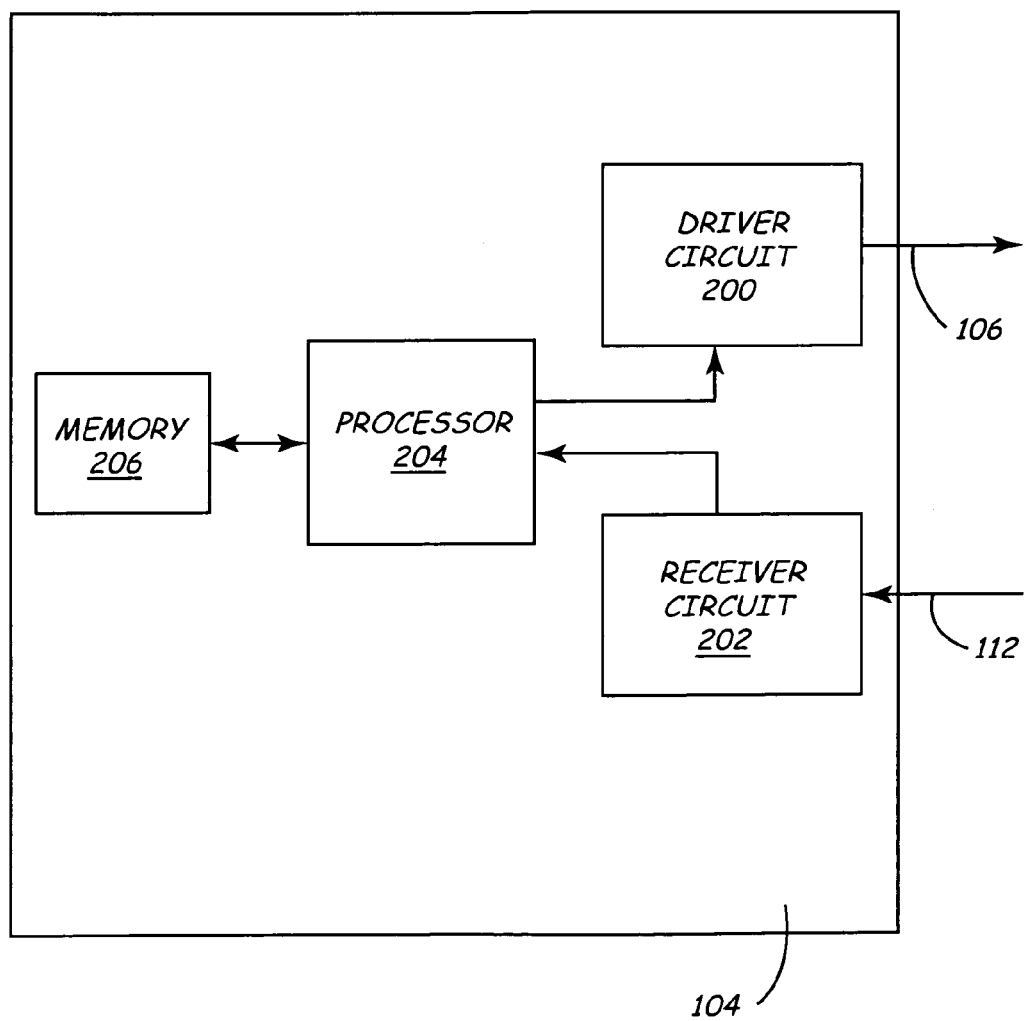
FIG. 2 illustrates a stylized block diagram of a controller of FIG. 1.

FIG. 2 illustrates a block diagram of one embodiment of the controller 104. Generally, the controller 104 is comprised of one or more driver circuits 200 and receiver circuits 202. The driver circuits 200 are generally responsible for providing the stimulating signals over the lines 106 to the electrodes 108. That is, a processor 204, operating under software or hardware control, may instruct the driver circuit 200 to produce a stimulating signal having a set of preselected, desired parameters, such as frequency, voltage and magnitude. The receiver circuits 202 are generally responsible for receiving signals over the lines 112 from the sensors 110, and processing those signals into a form, such as digital, which may be analyzed by the processor 204 and/or stored in a memory 206, such as a dynamic random access memory (DRAM). The memory 206 may also store software, which is used to control the operation of the processor 204.

Figure 3:
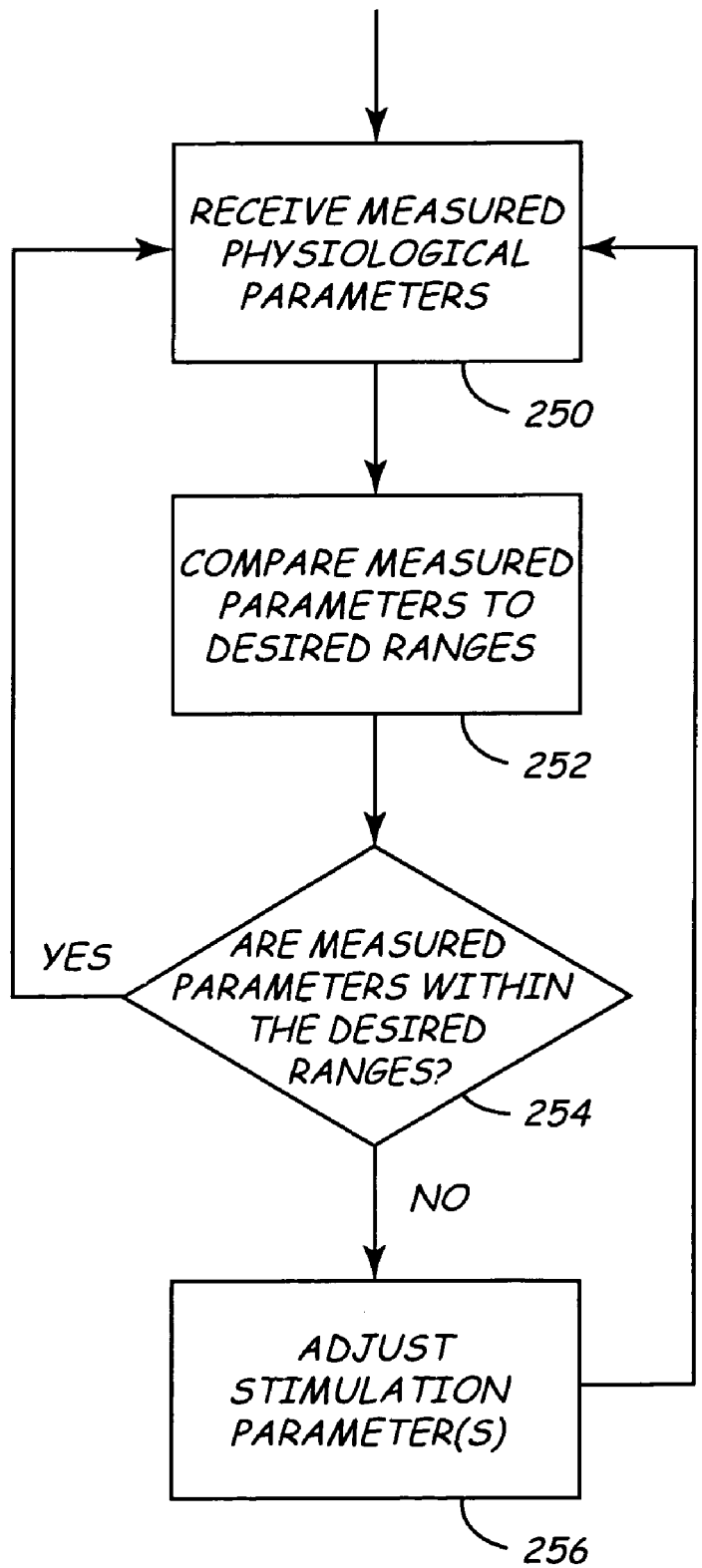
FIG. 3 illustrates a stylized flowchart of a control routine that may be performed by the controller of FIGS. 1 and 2.

The overall general operation of the controller 104 in automated, or "closed-loop", mode may be appreciated by reference to a flowchart depicted in FIG. 3. Those skilled in the art will appreciate that the flowchart illustrated herein may be used to represent either software that may be executed by the processor 204 or hardware configured to operate to perform the functions set forth in the flowchart. The process depicted in FIG. 3 begins at block 300 with the assumption that a cardiac event may have been detected either automatically or manually, but in any event, therapy is being administered by the controller 104.

At block 250, the processor 204 receives the measured physiological parameters via the receiver circuits 202. At block 252, the processor 204 compares the measured parameters to corresponding desired ranges. If the measure parameters are within the desired range, as determined at block 254, the processor 204 returns to block 250 and the process repeats. On the other hand, if the measured parameters fall outside the desired range, then the processor 204 at block 256 adjusts the stimulation parameter, which should result in the physiological parameters of the patient being adjusted to fall within the desired range. Thereafter, the process returns to block 250 and the process begins anew.

It should be appreciated that, owing to physiological differences between patients, an adjustment to the stimulation parameters may not produce an immediate, precise change in all patients. Rather, it is anticipated that each patient will respond substantially uniquely to variations in the stimulation parameters. Thus, it may be useful to add controllable variability to the operation of the feedback arrangement described herein. For example, it may be useful to control the rate at which the stimulation parameters are allowed to change, or to develop a histogram for a particular patient. The inventive system could include the ability to record parameters associated with the delivered stimulation such as pulse widths, frequencies, duty cycles, and time varying patterns. These parameters and the patient's response may be recorded in the memory 206, for example. Based on patient response, the efficacy of the stimulation can be evaluated so that the delivered stimulation can be adjusted to further improve cardiac efficiency. This "teaming" capability allows the system to optimize stimulation based on prior patient data so that treatment is automatically tailored to individual patient needs.

According to another aspect of the invention, electrical stimulation is provided when the tone in the paraspinal muscles is increasing, since this is an indicator of visceral complications. Detection of this increase in muscle tone could be accomplished using an externally-positioned strain gage, for example. Thus, electrical stimulation may be applied prior to the onset of actual ischemic so that cardiac tissue maybe protected in an anticipatory manner. Electrical stimulation may also continue while the muscle tone remains at a predetermined rigidity. In one embodiment, a rate-responsive sensor such as an accelerometer or other appropriate sensor may be used to sense the level of activity, and adjust the stimulation levels according to the activity level.

In one embodiment, a system could include the ability to record parameters associated with the delivered stimulation such as pulse widths, frequencies, duty cycles, waveform, and time varying patterns. Based on the detection of ischemic events as may be accomplished using ischemic detection systems of the type known in the art, the efficacy of the electrical stimulation may be evaluated so that the delivered stimulation may be adjusted during the next treatment session. This "learning" capability allows the system to optimize treatment based on prior patient data so that stimulation is automatically tailored to individual patient needs.

Figure 4:
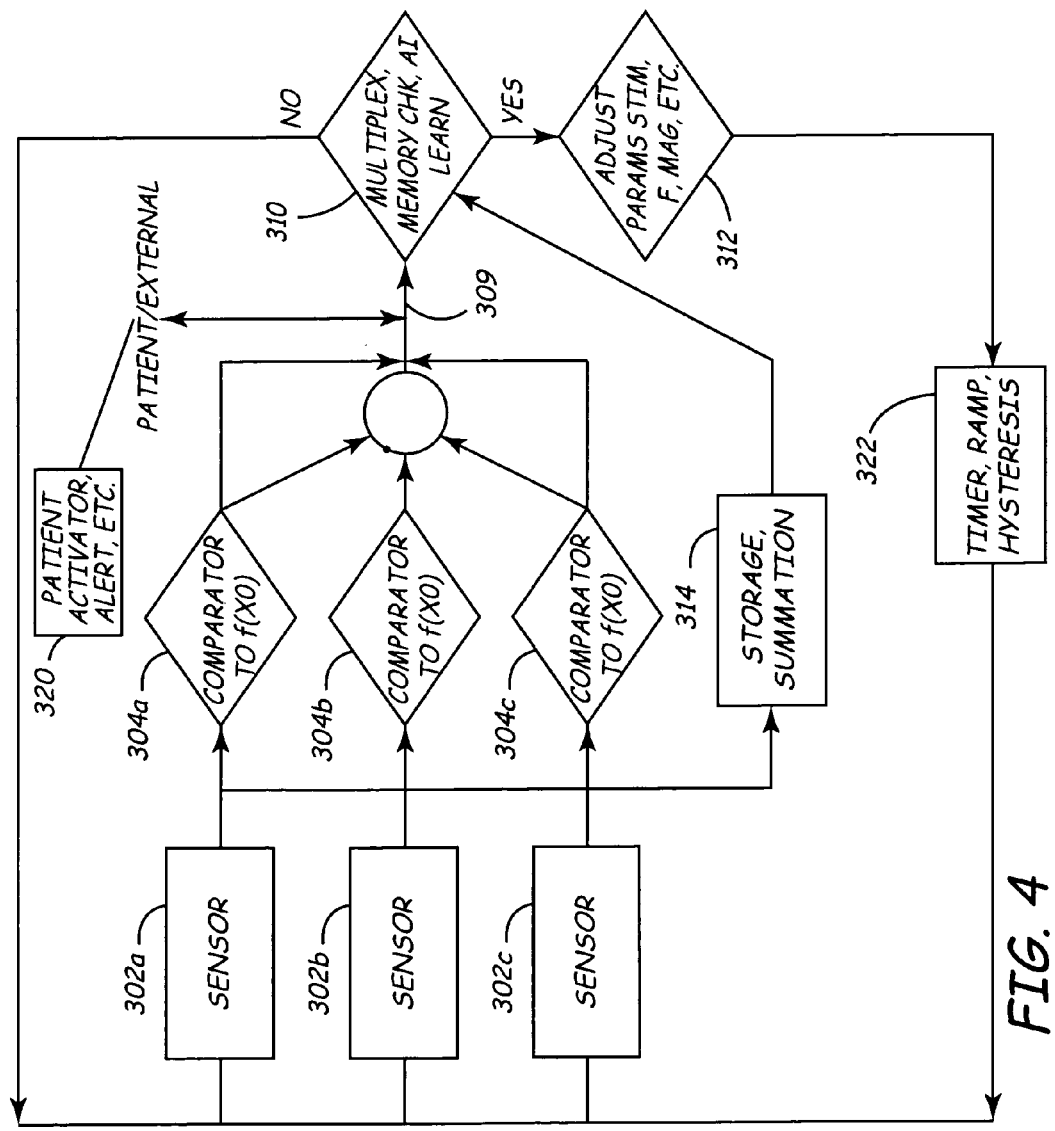
FIG. 4 is a flow diagram illustrating a system and method that may use multiple sensor measurements to perform this type of therapy.

In yet another embodiment of the invention, the system may utilized multiple scaled parameters to determine when cutaneous stimulation should be initiated. FIG. 4 is a flow diagram illustrating a system and method that may use multiple sensor measurements to perform this type of therapy. In FIG. 4, one or more sensors shown as sensors 302a through 302c are used to measure physiologic conditions. The measured signals may be compared against a threshold value by one or more comparators 304a through 304c. The results of the comparisons may be summed, or otherwise processed, with the processed data set being provided on line 309. If this result indicates that electrical stimulation is required, as determined by block 310, therapy is initiated. Therapy is initiated and controlled by a processing circuit, as represented by block 312. This processing circuit 312 provides the closed-loop feedback control used to modulate the level of therapy delivered. When therapy is to be discontinued, a ramp-down circuit shown in block 322 may be used to gradually discontinue the stimulation.

As discussed above, the electrical stimulation delivered by a cutaneous electrode system provides significant benefits when delivered prior to an anticipated cardiac insult, or an event that will induce ischemia. The benefits include minimizing or preventing acute infarct and reducing reperfusion arrhythmia. In one embodiment, the therapy is delivered thirty minutes or more prior to the anticipated on-set of an insult such as ischemia. As much as possible, the above therapies should be implemented prior to the insult. Some of the many exemplary embodiments included within the scope of the invention are shown in FIGS. 5A through 5E.

Figure 5A:
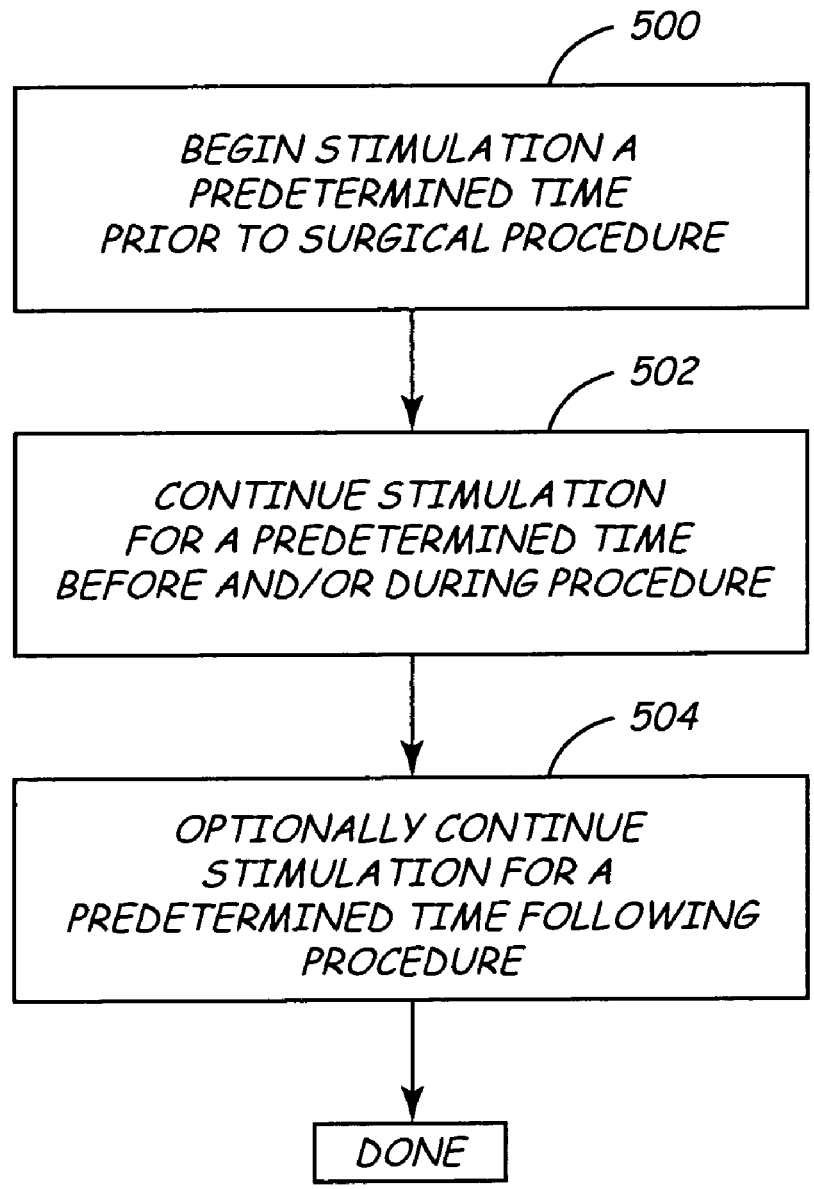
FIG. 5A is a flowchart illustrating delivery of cutaneous stimulation prior to planned cardiac interventions, like bypasses, angioplasties or stenting procedures.

FIG. 5A is a flowchart illustrating delivery of stimulation prior to planned cardiac interventions, like bypasses, angioplasties or stents (block 500). The stimulation could be applied for a predetermined time such as 30–120 minutes prior to the intervention (block 502). Stimulation may be continued for hours or days after the procedure to minimize adverse effects or to increase or even maximize patency of vessels (block 504).

Figure 5B:
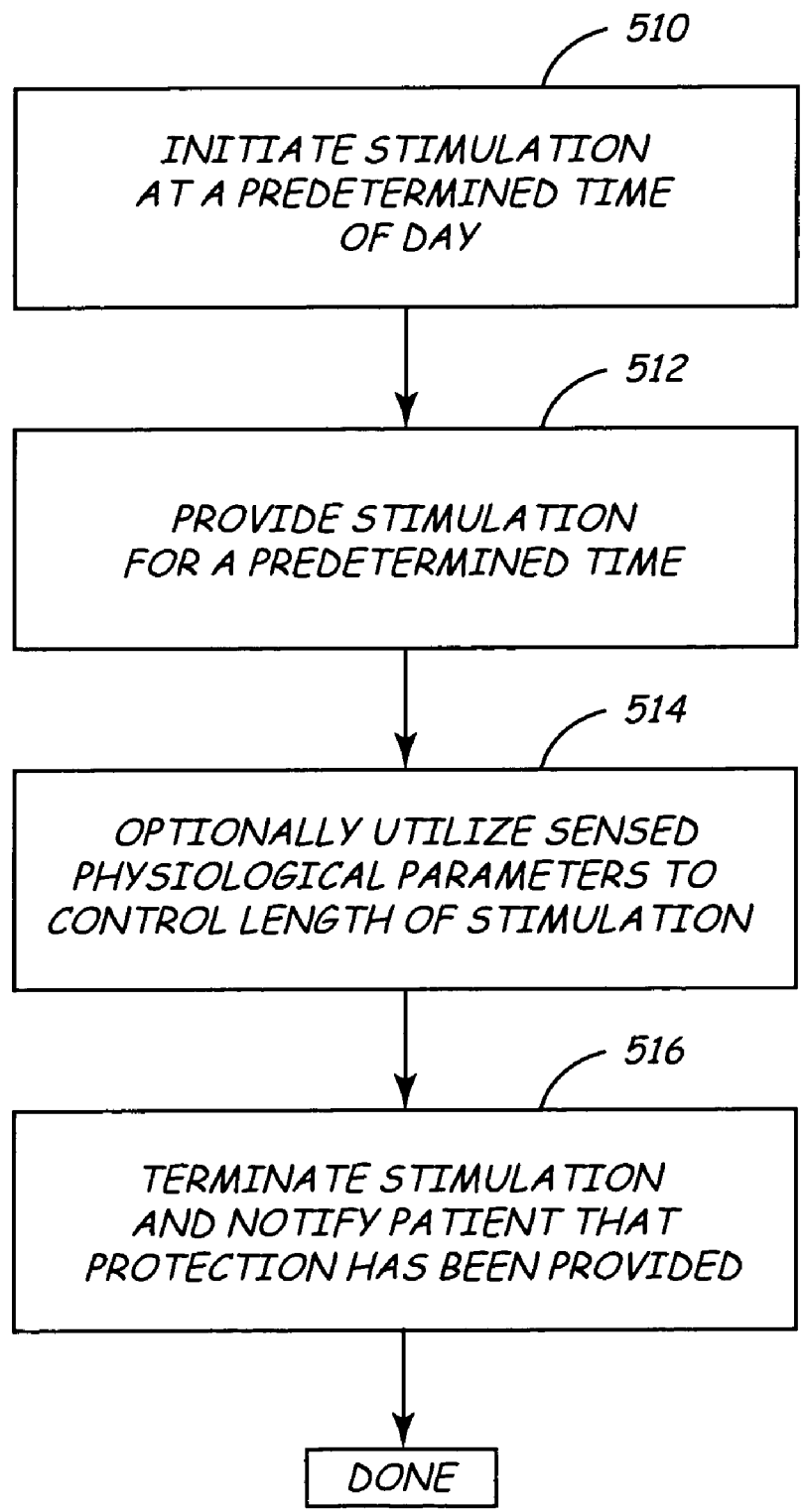
FIG. 5B is a flowchart illustrating delivery of cutaneous stimulation at a particular time of day.

FIG. 5B is a flowchart illustrating delivery of stimulation at a particular time of day (block 510). For example, stimulation may be provided when a patient wakes up in the morning. A timer may be utilized to initiate subthreshold stimulation, or alternatively, to initiate suprathreshold stimulation to provide paresthesia. After a predetermined time such as thirty minutes (block 512), or when sensed physiological parameters indicate that the appropriate level of cardiovascular protection has been established (block 514), the patient can be alerted (516). This could be accomplished, for example, by use of stimulation producing a stronger paresthesia.

Figure 5C:
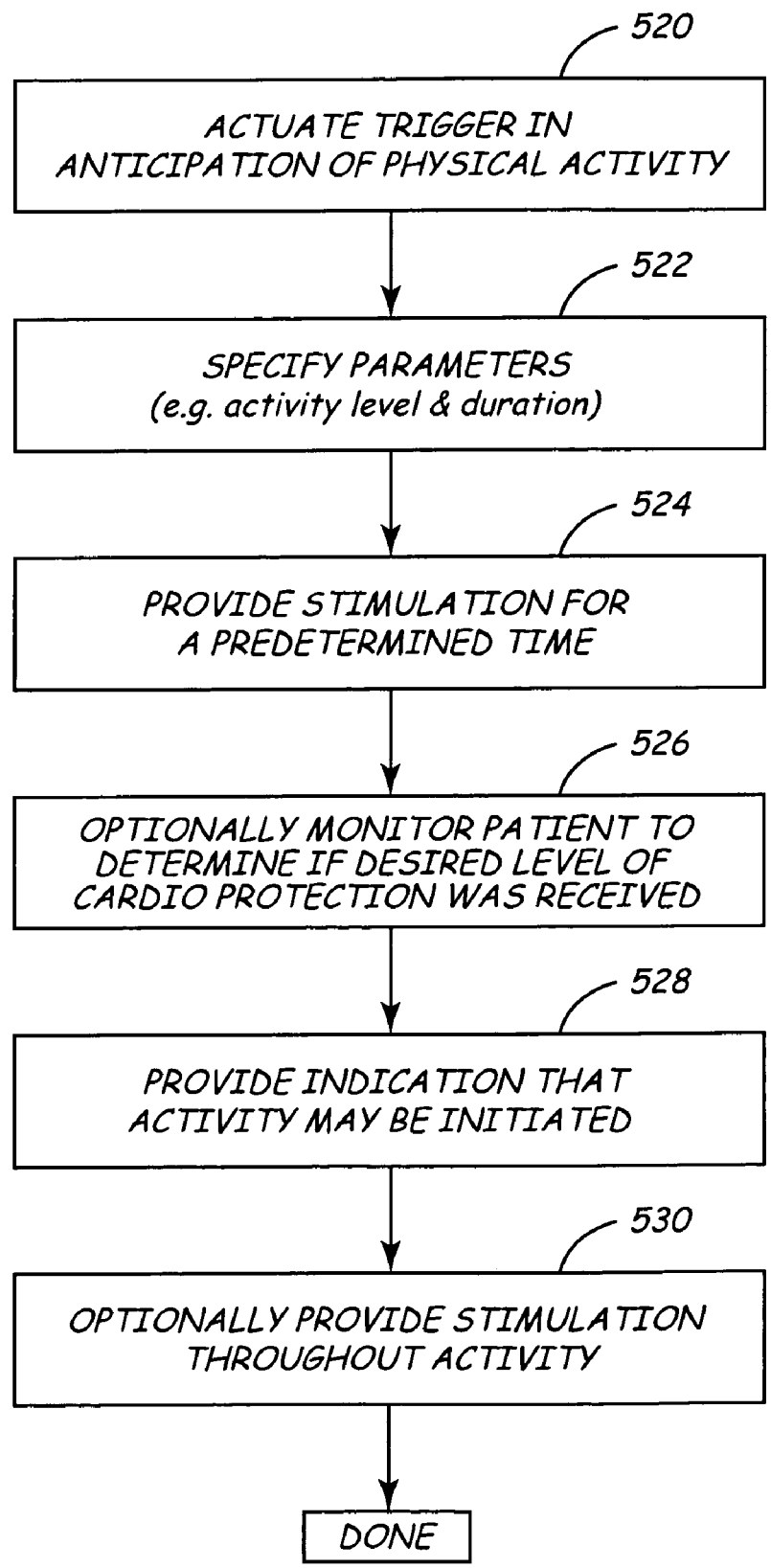
FIG. 5C is a flowchart illustrating delivery of cutaneous stimulation initiated because a patient anticipates physical activity and manually triggers therapy.

FIG. 5C is a flowchart illustrating delivery of stimulation initiated because a patient anticipates physical activity and manually triggers therapy (block 520). This by initiated by activating a power supply, for example.

In one embodiment, an expected intensity of the activity or other optional parameters may also be specified (block 522). After stimulation has been delivery for the specified time (block 524) and/or after the appropriate level of cardio protection has been determined to have been established (block 526), the device provides an indication that activity may be initiated (block 528). Stimulation may continue throughout the activity, if desired (block 530).

Figure 5D:
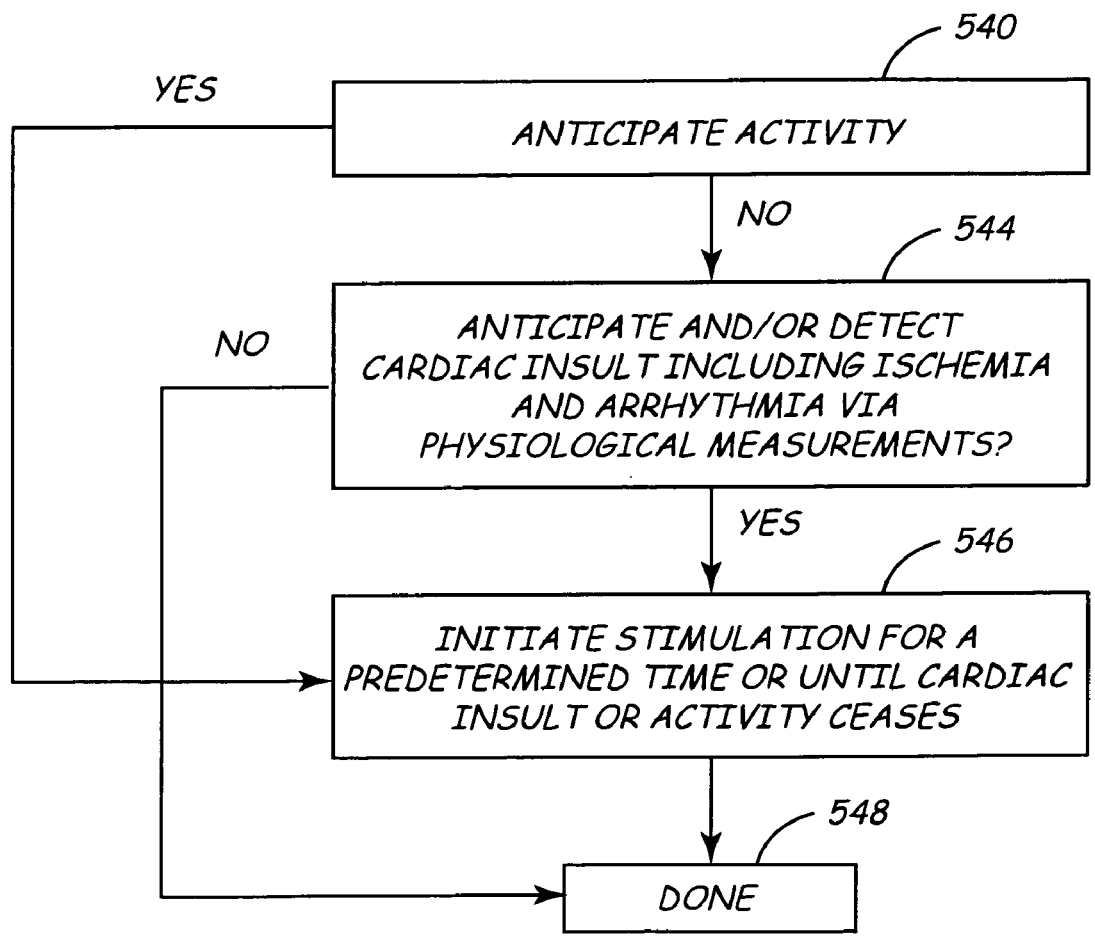
FIG. 5D is a flowchart illustrating cutaneous stimulation initiated at the first signs of activity in an anticipatory manner, or at the first indication that an insult may be predicted.

FIG. 5D is a flowchart illustrating stimulation initiated at the first signs of activity in an anticipatory manner (block 540), or at the first indication that ischemia, an episode of malignant ventricular arrhythmia, and/or any of the other insults discussed above may be anticipated (block 544). In the event that such activity is anticipated (blocks 540,544) then stimulation is initiated for a predetermined time or until cardiac insult of activity ceases (block 546). In the event that such activity is not anticipated (block 544) or ceases (block 546) then this embodiment of the invention is deemed done (block 548). The types of indications may be detected by one or more of the sensing mechanisms discussed above.

Figure 5E:
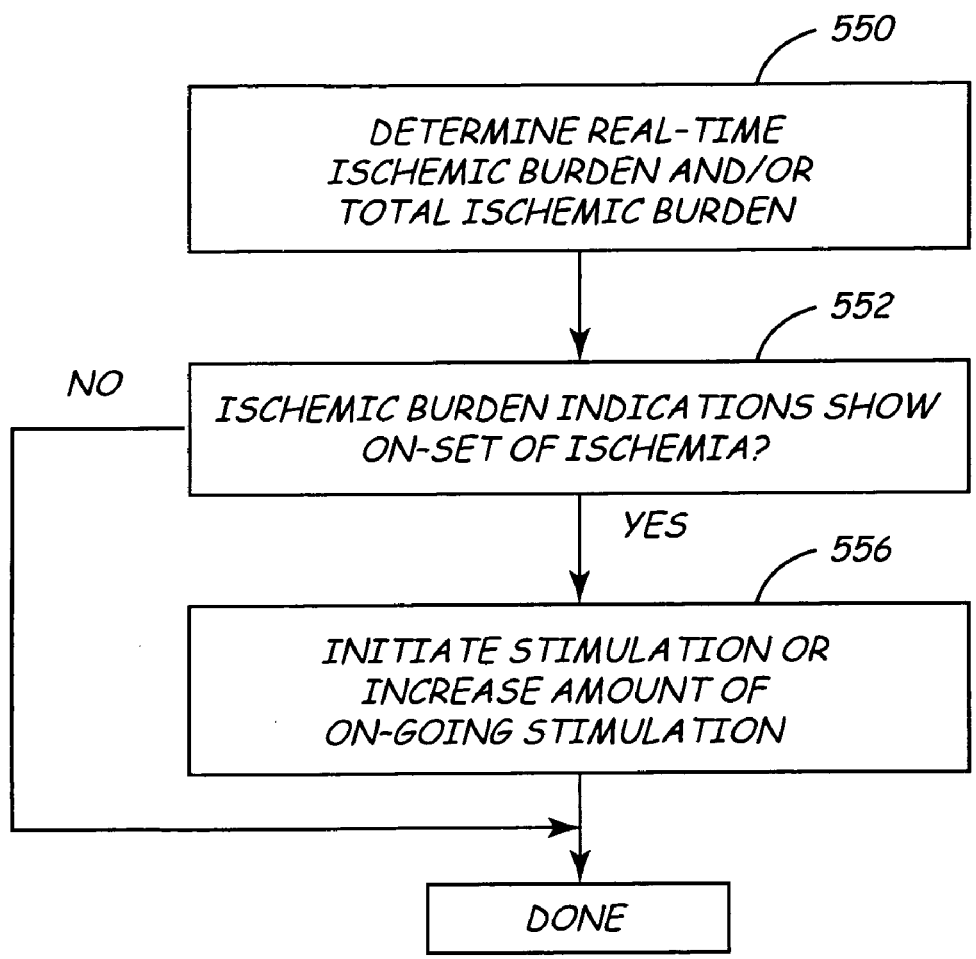
FIG. 5E is a flowchart illustrating cutaneous stimulation initiated based on a real time recording of ischemic burden and total ischemic burden.

FIG. 5E is a flowchart illustrating stimulation initiated based on a real time recording of ischemic burden and total ischemic burden (blocks 550 and 552). If desired, the prophylactic amount of stimulation could be increased if these measurements show increased ischemia in general (block 554), or an increased likelihood of the onset of ischemia (block 556).

Figure 5F:
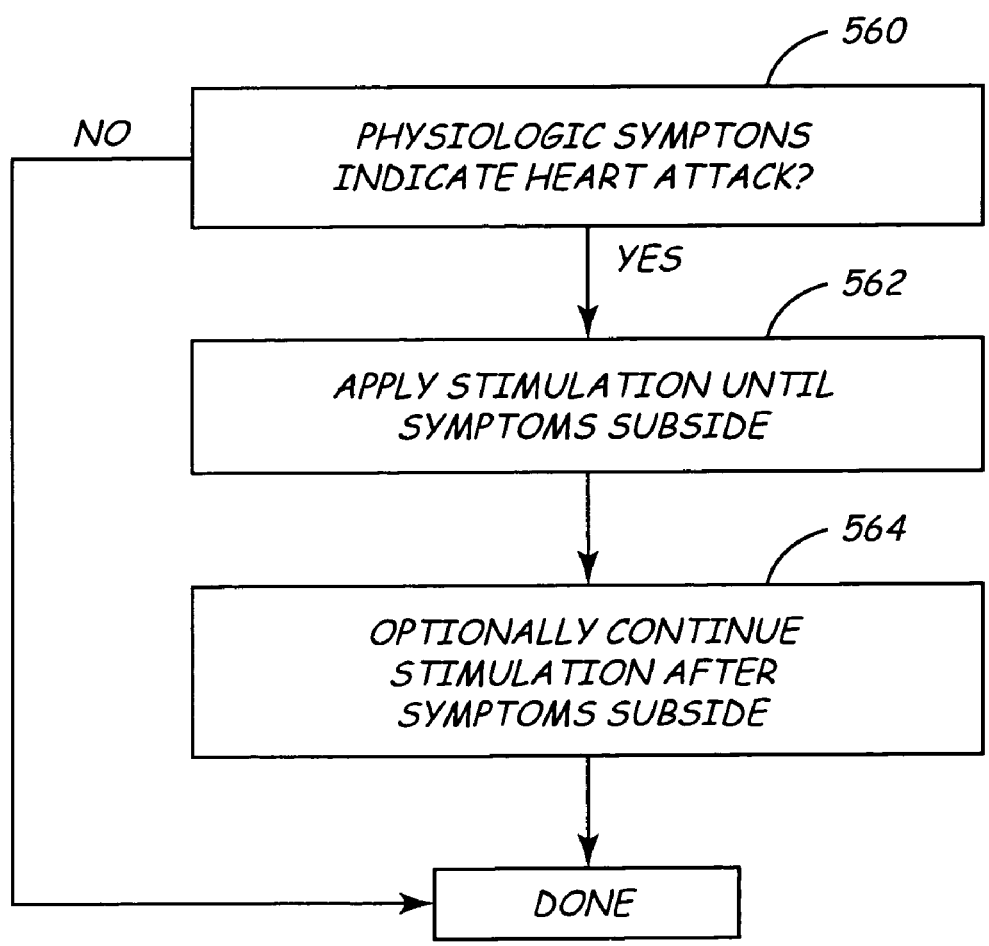
FIG. 5F illustrates the delivery of the therapy for protection during a suspected heart attack.

FIG. 5F illustrates the delivery of the therapy for protection during a suspected heart attack. To promote optimal recovery, stimulation may be applied by healthcare professionals as soon as possible in an appropriate form if a heart attack is even suspected (blocks 560 and 562). This is done using subcutaneous electrode systems discussed above. This stimulation may continue after the symptoms subside to further protect the cardiac tissue (564).

Table I illustrates some of the benefits associated with the subcutaneous electrical stimulation provided by the current invention. Table I further lists one or more physiological parameters that may be monitored when delivering stimulation to achieve a desired effect.

TABLE I

Benefits of Stimulation

| BENEFITS | PHYSIOLOGICAL PARAMETERS TRACKED |
|---|---|
| Prevention of VT/VF Incidents | Cardiac electrical, Cardiac Ishemia, Autonomic Activity, Physical Activity, Heart Rate and Rhythm |
| Reduce PVC's | Cardiac electrical, Cardiac Ishemia, Autonomic Activity, Physical Activity, Heart Rate and Rhythm |
| Reduce NSVT | Cardiac electrical, Cardiac Ishemia, Autonomic Activity, Physical Activity, Heart Rate and Rhythm |
| Lessen Cardiac Ischemia | Cardiac Ischemia; total ischemic burden, Physical Activity |
| Reduce Angina | Physical Activity, Cardiac Ishemia |
| Improved Exercise Tolerance | Physical Activity, respiration, blood chemistry |
| Rebalance Autonomic System | Cardiac electrical, Autonomic Activity, Hemodynamics |
| Improve Cardiac Performance: pump function, preload/afterload | Cardiac electrical and hemodynamics |
| Improve Cardiac Paracrine Function or Balance | Cardiac electrical and hemodynamics |
| Alter AV electrical function | Cardiac electrical |
| Restore heart rate Variability | Cardiac electrical, Autonomic Activity |
| Other | |

Other aspects of closed-loop operation in a neuromodulation system are described in commonly-assigned patent application Ser. No. 10/035,319 filed on even date herewith entitled "Closed-Loop Neuromodulation for Prevention and Treatment of Cardiac Conditions," which is incorporated herein by reference in its entirety.

As discussed in detail above, one aspect of the inventive system and method provides a system and method for employing closed-loop controls to initiate and deliver subcutaneous electrical stimulation. However, as also indicated above, the invention may also be utilized in an open-loop mode wherein the stimulation is trigger by the patient or another person. As shown in FIG. 3, the system may also provide the ability for the patient to activate the stimulation based on the onset of a physical condition such as exertion or pain. Patient-initiated therapy may be limited or controlled by a programmable feature as specified by a physician. A timer may also be provided to initiate and control therapy at one or more times during the day.

In one embodiment, a notification feature is provided to notify the patient and/or a physician of changing patient conditions indicative of increased ischemic risk. The invention may further include means to discontinue or limit therapy when closed-loop feedback techniques are leading to an undesirable situation.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for protecting cardiac tissue from a myocardial insult resulting in necrosis of myocardial tissue, comprising:
    identifying an occurrence of a myocardial insult capable of resulting in necrosis of myocardial tissue; and
    automatically delivering electrical stimulation cutaneously adjacent to one or more of the T1–T12 vertebrae or at upper cervical levels C1–C4 over the back of the head and neck in a patient's body using one or more electrodes positioned adjacent an external surface of the body in order to avoid necrosis of myocardial tissue due to the insult, wherein said one or more electrodes are spaced from myocardial tissue of the patient.

2. The method of claim 1, wherein identifying the occurrence of the insult further comprises identifying one or more symptoms of a heart attack.

3. The method of claim 1, further comprising identifying the severity of the insult.

4. The method of claim 3, wherein delivering electrical stimulation further comprises delivering electrical stimulation having an intensity based on the identified severity of the insult.

5. The method of claim 1, wherein the delivering electrical stimulation further comprises:
    storing data descriptive of the electrical stimulation;
    analyzing the effectiveness of the electrical stimulation; and
    adjusting the delivery of electrical stimulation in a subsequent delivery of electrical stimulation.

6. The method of claim 1, wherein delivering electrical stimulation further comprises delivering electrical stimulation for a period of time extending beyond a cessation of the insult.

7. The method of claim 1, wherein delivering electrical stimulation further comprises delivering electrical stimulation for a preselected duration of time.

8. The method of claim 1, wherein identifying the occurrence of the insult further comprises determining that a defibrillation shock has been administered.

9. The method of claim 1, wherein identifying the occurrence of the insult further comprises detecting myocardial ischemia.

10. The method of claim 1, wherein identifying the occurrence of the insult further comprises detecting an arrhythmic event.

11. The method of claim 1, wherein identifying the occurrence of the insult further comprises detecting non-sustained ventricular tachycardia.

12. The method of claim 1, wherein identifying the occurrence of the insult further comprises detecting precursors to a ventricular arrhythmia.

13. The method of claim 1, and further comprising sensing a physiologic parameter; and
adjusting delivery of electrical stimulation based on the sensed physiologic parameter.

14. The method of claim 13, wherein multiple physiologic parameters are sensed; and wherein delivery of electrical stimulation is adjusted based on the multiple physiologic parameters.

15. The method of claim 14, and further comprising obtaining an indication based on a weighting of the multiple physiologic parameters; and
adjusting delivery of the electrical stimulation based on the indication.

16. The method of claim 15, and further comprising providing a patient notification indicative of the cardiac insult.

17. An apparatus for protecting cardiac tissue from a myocardial insult resulting in necrosis of myocardial tissue, comprising:
at least one electrode positionable adjacent an external surface of a body and cutaneously adjacent to one or more of the T1–T12 vertebrae or at upper cervical levels C1–C4 over the back of the head and neck proximate to nerve tissue and spaced from myocardial tissue; and
a controller adapted to identify a cardiac insult and to automatically deliver electrical stimulation to the at least one electrode in order to avoid necrosis of myocardial tissue due to the insult.

18. The apparatus of claim 17, further comprising memory adapted to store data descriptive of the electrical stimulation, and wherein the controller is adapted to analyze the stored data and adjust electrical stimulation in response thereto.

19. The apparatus of claim 17, further comprising a sensor configured to detect a physiologic condition representative of an operating characteristic of the patients heart, and wherein the controller is adapted to deliver electrical stimulation to the at least one electrode based on an indication of the physiologic condition.

20. The apparatus of claim 19, wherein the controller includes a circuit to control delivery of electrical stimulation to the electrodes for a preselected duration of time.

21. A computer readable medium for storing instructions for performing a computer-implemented method to protect cardiac tissue from a myocardial insult resulting in necrosis of myocardial tissue, comprising:
software encoded instructions for identifying an occurrence of a myocardial insult; and
software encoded instructions automatically delivering electrical stimulation using one or more electrodes positioned adjacent an external surface of the body in order to avoid necrosis of myocardial tissue due to the insult.

22. A medium according to claim 21, wherein the software encoded instructions for identifying the occurrence of the insult further comprises software encoded instructions for identifying one or more symptoms of a heart attack.

23. A medium according to claim 21, further comprising identifying the severity of the insult which produces said necrosis of myocardial tissue.

24. A medium according to claim 23, wherein the software encoded instructions for delivering electrical stimulation further comprises software encoded instructions for delivering electrical stimulation having an intensity based on the identified severity of the insult.

25. A medium according to claim 21, wherein the software encoded instructions for delivering electrical stimulation further comprises:
software encoded instructions for storing data descriptive of the electrical stimulation;
software encoded instructions for analyzing the effectiveness of the electrical stimulation; and
software encoded instructions for adjusting the delivery of electrical stimulation in a subsequent delivery of electrical stimulation.

* * * * *

UNITED STATES PATENT AND TRADEMARK OFFICE
CERTIFICATE OF CORRECTION

PATENT NO. : 7,010,345 B2 Page 1 of 1
APPLICATION NO. : 09/999723
DATED : March 7, 2006
INVENTOR(S) : Thomas J. Mullen et al.

It is certified that error appears in the above-identified patent and that said Letters Patent is hereby corrected as shown below:

Col. 13, line 36, please delete "head and neck proximate to nerve tissue and spaced" and insert --head and neck and spaced--.

Signed and Sealed this

Twenty-sixth Day of December, 2006

JON W. DUDAS
*Director of the United States Patent and Trademark Office*